United States Patent
Viswanathan et al.

(10) Patent No.: US 8,024,024 B2
(45) Date of Patent: Sep. 20, 2011

(54) REMOTE CONTROL OF MEDICAL DEVICES USING REAL TIME LOCATION DATA

(75) Inventors: Raju R. Viswanathan, St. Louis, MO (US); Walter M. Blume, St. Louis, MO (US); Ilker Tunay, St. Louis, MO (US); Charidimos E. Gasparakis, St. Louis, MO (US); Gareth T. Munger, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 514 days.

(21) Appl. No.: 12/163,693

(22) Filed: Jun. 27, 2008
(Under 37 CFR 1.47)

(65) Prior Publication Data
US 2009/0177037 A1    Jul. 9, 2009

Related U.S. Application Data

(60) Provisional application No. 60/946,709, filed on Jun. 27, 2007.

(51) Int. Cl.
*A61B 5/05* (2006.01)
*A61B 1/00* (2006.01)
(52) U.S. Cl. ........................ 600/407; 600/118
(58) Field of Classification Search .................. 600/300, 600/325, 327, 332, 337, 407, 414, 423–424, 600/426, 462–471, 478, 486–488, 505, 508–509, 600/117–118, 129; 604/21–22; 606/14–15, 606/21; 607/9, 17–18, 29, 113, 122–126
See application file for complete search history.

(56) References Cited

U.S. PATENT DOCUMENTS

| | | | |
|---|---|---|---|
| 5,438,169 A * | 8/1995 | Kennedy et al. | 181/102 |
| 5,654,864 A | 8/1997 | Ritter et al. | |
| 5,931,818 A | 8/1999 | Werp et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,171,304 B1 * | 1/2001 | Netherly et al. | 606/32 |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |

(Continued)

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

*Primary Examiner* — Francis Jaworski
(74) *Attorney, Agent, or Firm* — Harness, Dickey & Pierce, P.L.C.

(57) ABSTRACT

A method of determining the quality of contact between a remotely navigated medical device and a cyclically moving anatomical structure includes measuring movement of the device, and processing the measured movement of the device to determine the contact between the device and the moving anatomical structure.

8 Claims, 4 Drawing Sheets

U.S. PATENT DOCUMENTS

| | | |
|---|---|---|
| 6,304,768 B1 | 10/2001 | Blume et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,755,816 B2 | 6/2004 | Ritter et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al |
| 7,248,914 B2 | 7/2007 | Hastings et al. |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,341,063 B2 | 3/2008 | Garibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 7,558,402 B2 * | 7/2009 | Zhou et al. .................... 382/103 |
| 7,577,281 B2 * | 8/2009 | Nishiura ....................... 382/128 |
| 7,742,250 B2 * | 6/2010 | Nelson et al. ................... 360/31 |
| 2001/0038683 A1 | 11/2001 | Ritter et al. |
| 2002/0019644 A1 | 2/2002 | Hastings et al. |
| 2002/0100486 A1 | 8/2002 | Creighton, IV et al. |
| 2003/0125752 A1 | 7/2003 | Werp et al. |
| 2003/0130576 A1 * | 7/2003 | Seeley et al. .................... 600/426 |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0059237 A1 * | 3/2004 | Narayan et al. ................ 600/509 |
| 2004/0064153 A1 | 4/2004 | Creighton, IV et al. |
| 2004/0068173 A1 | 4/2004 | Viswanathan |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0249262 A1 | 12/2004 | Werp et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0065435 A1 | 3/2005 | Rauch et al. |
| 2005/0096589 A1 | 5/2005 | Shachar |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0256398 A1 | 11/2005 | Hastings et al. |
| 2005/0273130 A1 | 12/2005 | Sell |
| 2006/0004382 A1 | 1/2006 | Hogg et al. |
| 2006/0009735 A1 | 1/2006 | Viswanathan et al. |
| 2006/0025676 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036125 A1 | 2/2006 | Viswanathan et al. |
| 2006/0036163 A1 | 2/2006 | Viswanathan |
| 2006/0036213 A1 | 2/2006 | Viswanathan et al. |
| 2006/0041178 A1 | 2/2006 | Viswanathan et al. |
| 2006/0041179 A1 | 2/2006 | Viswanathan et al. |
| 2006/0041180 A1 | 2/2006 | Viswanathan et al. |
| 2006/0041181 A1 | 2/2006 | Viswanathan et al. |
| 2006/0041245 A1 | 2/2006 | Ferry et al. |
| 2006/0058618 A1 * | 3/2006 | Nishiura ....................... 600/407 |
| 2006/0058646 A1 | 3/2006 | Viswanathan |
| 2006/0074297 A1 | 4/2006 | Viswanathan |
| 2006/0079745 A1 | 4/2006 | Viswanathan |
| 2006/0079812 A1 | 4/2006 | Viswanathan |
| 2006/0094956 A1 | 5/2006 | Viswanathan |
| 2006/0100505 A1 | 5/2006 | Viswanathan |
| 2006/0114088 A1 | 6/2006 | Shachar |
| 2006/0116633 A1 | 6/2006 | Shachar |
| 2006/0122526 A1 * | 6/2006 | Berenfeld et al. ............ 600/515 |
| 2006/0144407 A1 | 7/2006 | Aliberto et al. |
| 2006/0144408 A1 | 7/2006 | Ferry |
| 2006/0270915 A1 | 11/2006 | Ritter et al. |
| 2006/0270948 A1 | 11/2006 | Viswanathan et al. |
| 2006/0278248 A1 | 12/2006 | Viswanathan |
| 2007/0010742 A1 * | 1/2007 | Torp et al. ..................... 600/437 |
| 2007/0016010 A1 | 1/2007 | Creighton et al. |
| 2007/0016131 A1 | 1/2007 | Munger et al. |
| 2007/0019330 A1 | 1/2007 | Wolfersberger |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0032727 A1 * | 2/2007 | Omata ........................ 600/481 |
| 2007/0032746 A1 | 2/2007 | Sell |
| 2007/0038064 A1 | 2/2007 | Creighton, IV |
| 2007/0038065 A1 | 2/2007 | Creighton, IV et al. |
| 2007/0038074 A1 | 2/2007 | Ritter et al. |
| 2007/0038410 A1 | 2/2007 | Tunay |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055130 A1 | 3/2007 | Creighton, IV |
| 2007/0060829 A1 | 3/2007 | Pappone |
| 2007/0060916 A1 | 3/2007 | Pappone |
| 2007/0060962 A1 | 3/2007 | Pappone |
| 2007/0060966 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0073288 A1 | 3/2007 | Hall et al. |
| 2007/0123964 A1 | 5/2007 | Davies et al. |
| 2007/0135804 A1 | 6/2007 | Ritter |
| 2007/0137656 A1 | 6/2007 | Viswanathan |
| 2007/0146106 A1 | 6/2007 | Creighton, IV |
| 2007/0149946 A1 | 6/2007 | Viswanathan |
| 2007/0161882 A1 * | 7/2007 | Pappone ....................... 600/374 |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197901 A1 | 8/2007 | Viswanathan |
| 2007/0197906 A1 | 8/2007 | Ritter |
| 2007/0225589 A1 | 9/2007 | Viswanathan |
| 2007/0250041 A1 | 10/2007 | Werp |
| 2007/0270686 A1 | 11/2007 | Ritter et al. |
| 2008/0004595 A1 | 1/2008 | Viswanathan |

| | | | | | | |
|---|---|---|---|---|---|---|
| 2008/0006280 A1 | 1/2008 | Alberto et al. | | 2008/0103398 A1* | 5/2008 | Huang .......................... 600/500 |
| 2008/0015427 A1 | 1/2008 | Kastelein et al. | | 2008/0114335 A1 | 5/2008 | Flickinger et al. |
| 2008/0015670 A1 | 1/2008 | Pappone | | 2008/0132910 A1 | 6/2008 | Pappone |
| 2008/0016677 A1 | 1/2008 | Creighton, IV | | 2008/0200913 A1 | 8/2008 | Viswanathan |
| 2008/0016678 A1 | 1/2008 | Creighton, IV et al. | | 2008/0208912 A1 | 8/2008 | Garibaldi |
| 2008/0039705 A1 | 2/2008 | Viswanathan | | 2008/0228065 A1 | 9/2008 | Viswanathan et al. |
| 2008/0039830 A1 | 2/2008 | Munger et al. | | 2008/0228068 A1 | 9/2008 | Viswanathan et al. |
| 2008/0043902 A1 | 2/2008 | Viswanathan | | 2008/0242976 A1* | 10/2008 | Robertson et al. ............ 600/425 |
| 2008/0045892 A1 | 2/2008 | Ferry et al. | | 2008/0287909 A1 | 11/2008 | Viswanathan et al. |
| 2008/0047568 A1 | 2/2008 | Ritter et al. | | 2008/0294232 A1 | 11/2008 | Viswanathan |
| 2008/0055239 A1 | 3/2008 | Garibaldi et al. | | 2008/0312673 A1 | 12/2008 | Viswanathan et al. |
| 2008/0058608 A1 | 3/2008 | Garibaldi et al. | | 2008/0319303 A1 | 12/2008 | Sabo et al. |
| 2008/0058609 A1 | 3/2008 | Garibaldi et al. | | 2009/0131802 A1* | 5/2009 | Fulghum et al. ............. 600/478 |
| 2008/0058963 A1 | 3/2008 | Garibaldi et al. | | 2009/0259149 A1* | 10/2009 | Tahara et al. ..................... 601/2 |
| 2008/0059598 A1 | 3/2008 | Garibaldi et al. | | 2010/0222671 A1* | 9/2010 | Cohen et al. ................... 600/424 |
| 2008/0064933 A1 | 3/2008 | Garibaldi et al. | | 2010/0317981 A1* | 12/2010 | Grunwald ..................... 600/509 |
| 2008/0064969 A1 | 3/2008 | Kastelein | | 2010/0331950 A1* | 12/2010 | Strommer ..................... 623/1.11 |
| 2008/0065061 A1 | 3/2008 | Viswanathan | | 2011/0039294 A1* | 2/2011 | Wang et al. ..................... 435/29 |
| 2008/0077007 A1 | 3/2008 | Hastings et al. | | 2011/0106070 A1* | 5/2011 | Fischer et al. ................. 606/21 |
| 2008/0092993 A1 | 4/2008 | Creighton, IV | | | | |
| 2008/0097200 A1 | 4/2008 | Blume et al. | | * cited by examiner | | |

REMOTE CONTROL OF MEDICAL DEVICES USING REAL TIME LOCATION DATA

CROSS-REFEENCE TO RELATED APPLICATIONS

This application claims priority to U.S. Provisional Patent Application Ser. No. 60/946,709, filed Jun. 27, 2007. The disclosure of the above-referenced application is incorporated herein by reference.

BACKGROUND

This invention relates to remote navigation of medical devices, and in particular to improved control over the remote navigation of medical devices using real time location data.

In remote medical navigation procedures, the distal end of an elongate medical device is introduced into the subject's body (typically the vessels of the subjects circulatory system), and the distal end of the device is oriented and advanced through the body to a desired location. An example of remote navigation system for conducting remote medical navigation procedures is the Niobe® magnetic navigation system available from Stereotaxis, Inc., St. Louis, Mo. This system allows the user to orient the distal end of a compatible device in a selected direction through the application of a magnetic field from one or more external source magnets, and selectively advance the medical device in the selected direction. These magnetic navigation systems allow for fast and easy navigation of a device through a subject's body. Other types of remote navigation systems could employ mechanical systems, electrostrictive systems, hydraulic systems, and pneumatic systems for remotely orienting the distal end of a medical device.

Remote navigation systems are frequently used in conjunction with a localization system that can determine the position and the orientation of the medical device. These localization systems include magnetic localization systems and electropotential localization systems. The localization can be provided in real time, or it can be gated, for example in coordination with the respiratory or cardiac cycle. This localization information can be used in an iterative feedback algorithm for reaching an arbitrary target, or in an algorithm for making small moves along a desired user-defined path.

SUMMARY

Embodiments of the present invention provide for enhanced remote control of remote medical device using real time location data. In accordance with one embodiment, when a catheter or other device is in contact with a structure such as a cardiac wall, the position is monitored in real time, and through analysis of the tip location data, it is possible to estimate the periodicities of the cardiac cycle and of the respiration cycle. The resulting identified periodicity can be used to gate the navigation system for respiration, for instance during targeting.

In accordance with another embodiment of this invention, real-time tip location data can also be used to estimate the qualitative extent of contact with an anatomical structure. The inventors have discovered that a catheter with a soft shaft (such as magnetic catheters) that is engaged in wall contact will tend to maintain tip contact at a fixed location relative to the cardiac wall during motion of the wall, since the shaft can easily buckle or deform to permit this. Accordingly, the extent of motion of the tip over the cardiac cycle will be largest when contact is very consistent. This can be used in several ways to estimate the quality of contact of the device with the anatomical structure.

One way of estimating the quality of contact is using the oscillation amplitude. Tracking the oscillation of the difference $[x_{real}-x_{gated}]$ over a few cardiac cycles, where the three dimensional vectors are defined such that $x_{gated}$ is always the most recent gated location (gated to the cardiac cycle) and $x_{real}$ is the real-time location. If contact is temporarily lost for a portion of time between successive cycles, the amplitude of the oscillation will display a "truncated" or flat behavior over such time intervals, where the catheter location will stay relatively constant, and this can be detected from signal analysis to assess stability of contact.

Another way of estimating the quality of contact is using positional covariance. If $x_{mean}$ is the mean location over a cardiac cycle, set $X=(x-x_{mean})$ and form the 3×3 covariance matrix C with entries $C_{ij}=\langle X_i X_j \rangle$ where the average $\langle \, \rangle$ is taken over a cardiac cycle (or over several cycles). Let a, b and c be the eigenvectors of C, with corresponding eigenvalues $e_a$, $e_b$, $e_c$. These eigenvectors and eigenvalues define the covariance ellipsoid associated with the motion of the catheter tip. A soft catheter that maintains good contact with a given target location on the cardiac wall over the cardiac cycle will have larger values of $(e_a, e_b, e_c)$ than a catheter that is in inconsistent/unstable contact; thus for example, $D=(e_a+e_b+e_c)$ can be used as a measure of contact. Alternatively or in addition, the difference between maximum and minimum eigenvalues $(e_{max}-e_{min})$ can be used as a measure of contact; in some situations a larger eigenvalue difference can represent greater relative motion along one direction, thus characterizing the local cardiac wall motion. A catheter tip in stable contact with such a cardiac wall location would move with the cardiac wall through the cardiac cycle.

To enhance contact between the medical device and the tissue, the surface normal n to the cardiac wall can be used in order to torque the device tip into the wall. For example, with a magnetic navigation system, the magnetic field can be rotated about an axis defined by $v=t\times n$ in order to push the device tip into the wall, where t is the device tip orientation. In this case, let a be the eigenvector of C that has the largest dot product with n; then a can be used in some cases in place of n to define the axis of rotation v.

Another way of estimating the quality of contact is using orientational covariance. If $t_{mean}$ is the mean tip orientation over a cardiac cycle, and $T=(t-t_{mean})$, a covariance matrix M can be formed with entries $M_{ij}=\langle M_i M_j \rangle$ (average taken over a cardiac cycle), and as with the positional covariance matrix discussed above, the eigenvalues and eigenvectors of M can be used to assess extent of contact. Analogously to the contact measures based on positional covariance eigenvalues, measures based on the orientational covariance eigenvalues such as the magnitude of the summed eigenvalues, or the difference between maximum and minimum eigenvalues, can be used to assess stability of cardiac contact.

Another method of measuring contact stability is to perform a frequency analysis of catheter tip motion. The frequency spectrum of the motion of a catheter tip that is in firm contact with the cardiac wall will have a dominant peak at the frequency of the cardiac cycle. Thus, the ratio of the peak (maximum) in the Fourier transform of the catheter tip location over a period of time to the next smaller peaks in the frequency spectrum can provide a measure of contact. Other measures based on the frequency spectrum such as the spread in frequency between specified peak threshold values, or a variety of other such possible measures can also be used.

Another way of estimating the quality of contact is using perturbation. A control variable of the navigation system (for example magnetic field direction, or catheter insertion length) can be perturbed or changed by a small amount, and the resulting change in a contact measure (such as one of the eigenvalue-based measures discussed above) can be determined. Thus for instance if contact is found to be enhanced by a small amount, a larger change in the same sense of the corresponding control variables can be applied to further enhance contact.

Another way of estimating the quality of contact is using unipolar voltage: If unipolar intracardiac ECG voltage information is available in real-time, its magnitude can be used to sense proximity to the wall. In particular, its behavior over a cardiac cycle or a several cycles can be analyzed as in the methods above (except that voltage values would be used instead of positional data) in order to assess stability, with the difference that the variation in voltage will be the smaller when contact is better.

Still another way of estimating the quality of contact is using a mapped mechanical model. A cardiac mechanical motion model is constructed by mapping over a "coarse" set of cardiac wall locations with a localized mapping catheter, so that the range of wall motion at every map point is recorded, the range of mechanical motion at intermediate points can be estimated, for example by interpolation. When the catheter is later placed at such an intermediate location, the range of motion as seen in the real-time location data can be compared with the expected range of motion in order to assess quality of contact.

Thus the various embodiments of this invention provide for the improved control, and in particular for enhanced measure of contact, and thus control of contact, of a remote medical navigation system. These and other features and advantages will be in part apparent, and in part pointed out hereinafter.

BRIEF DESCRIPTION OF THE DRAWINGS

Corresponding reference numerals indicated corresponding parts throughout the several views of the drawings.

DETAILED DESCRIPTION

Remote navigation systems have been used in recent years in the interventional treatment of various medical conditions such as, for example, cardiac arrythmias. An example of remote navigation system for conducting remote medical navigation procedures is the Niobe® magnetic navigation system available from Stereotaxis Inc., St. Louis, Mo. This system allows the user to orient the distal end of a compatible device in a selected direction through the application of a magnetic field from one or more external source magnets, and selectively advance the medical device in the selected direction. These magnetic navigation systems allow for fast and easy navigation of a device through a subject's body. Other types of remote navigation systems could employ mechanical systems, electrostrictive systems, hydraulic systems, and pneumatic systems for remotely orienting the distal end of a medical device. Often, during the use of a medical device navigated with a remote navigation system, it is useful to determine the extent of contact of the medical device with an anatomical organ such as the heart. Such a measure can be useful in further enhancing contact so that the medical procedure, for example intracardiac Radio-Frequency ablation, can be better performed.

Embodiments of the present invention provide for enhanced remote control of remote medical device using real time location data. In accordance with one embodiment, when a catheter or other device is in contact with a structure such as a cardiac wall, the position is monitored in real time, and through analysis of the tip location data, it is possible to estimate the periodicities of the cardiac cycle and of the respiration cycle. The resulting identified periodicity can be used to gate the navigation system for respiration, for instance during targeting. The remote navigation system interfaces with a localization system that determines real-time location data and provides it to the remote navigation system. The localization system can be an electromagnetic localization system (such as the Carto™ system manufactured by Biosense Webster Inc.) or an electric field-based localization system (such as the NavX™ system manufactured by St. Jude Medical), or be based on other modalities such as ultrasound localization. The remote navigation system can use the real-time device location data that it receives from the localization system in several ways. In particular, the present invention discusses methods of determining and enhancing contact stability based on such real-time location data (as generally used here, "location data" can be a combination of positional and orientational data).

Figure 6:
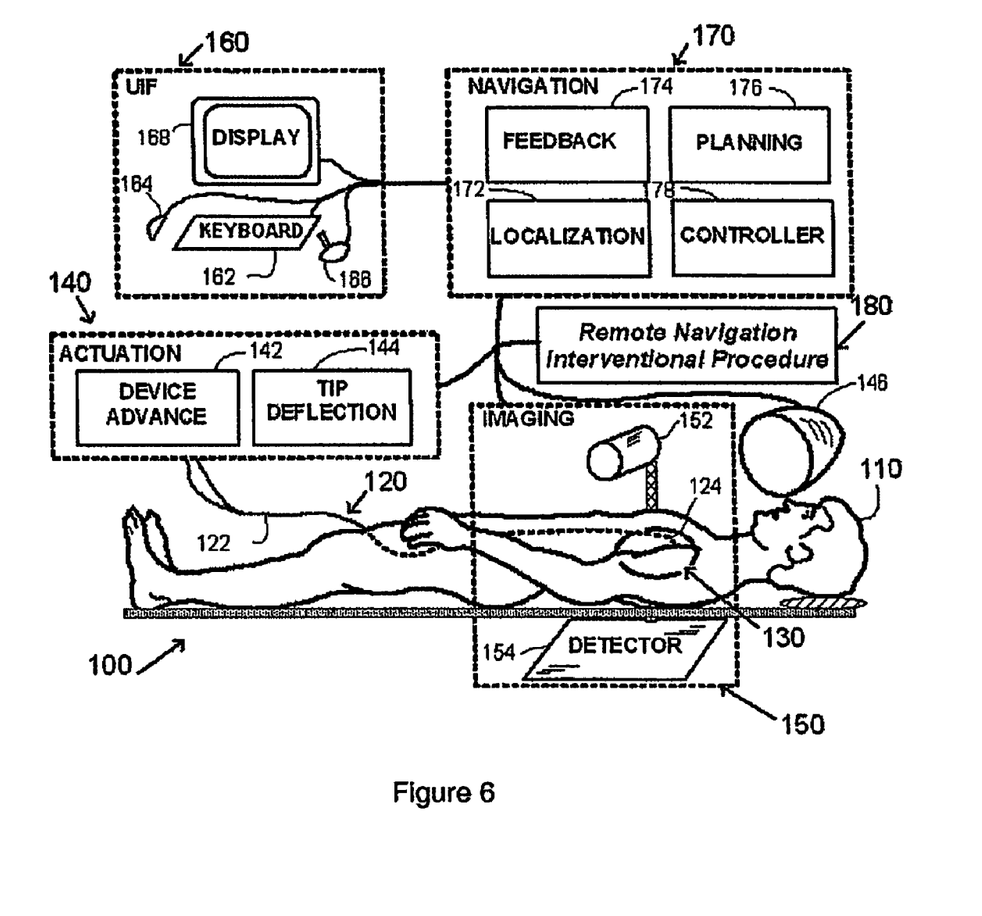
FIG. 6 is a schematic diagram of a remote navigation system, also showing a localization system or sub-system, that implements the real-time contact evaluation and control specified in the disclosure.

FIG. 6 illustrates in schematic form a remote navigation system for performing a remote navigation interventional procedure. As shown there, a patient 110 is positioned within a remotely actuated, computer controlled interventional system 100. An elongated navigable medical device 120 having a proximal end 122 and a distal end 124 is provided for use in the interventional system 100 and the medical device is inserted into a blood vessel of the patient and navigated to an intervention volume 130. A means of applying force or torque to advance or orient the device distal end 124 is provided, as illustrated by actuation block 140 comprising a component 142 capable of precise proximal device advance and retraction and a tip deflection component 144. The actuation sub-system for tip deflection may be one of (i) a robotically controlled mechanical pull-wire system; (ii) a magnetic system, consisting of external magnets for applying a magnetic field and at least one magnet in the distal portion of the interventional device for steering the device in response to the applied magnetic field; (iii) an electrostrictive system; (iv) a magnetostrictive system; (v) a hydraulic or pneumatic system; or (vi) other navigation system as known in the art. For illustration of a preferred embodiment, in magnetic navigation a magnetic field externally generated by magnet(s) assembly 146 orients a small magnetically responsive element (not shown) located at or near the device distal end 124. Real time information is provided to the physician by an imaging sub-system 150, for example an x-ray imaging chain comprising an x-ray tube 152 and a digital x-ray detector 154, to facilitate planning and guidance of the procedure.

Additional real-time information such as distal tip position and orientation may be supplied by use of a three-dimensional (3D) device localization sub-system such as comprising one or more electromagnetic wave receivers located at the device distal end (not shown), and associated external electromagnetic wave emitters (not shown); or other localization device with similar effect such as an electric field-based localization system that measures local fields induced by an externally applied voltage gradient. In the latter case the conducting body of a wire within the device itself carries the signal recorded by the tip electrode to a proximally located localization system. The real-time location information provided by the localization sub-system can be used for device contact assessment and control, as described further below.

The physician provides inputs to the navigation system through a user interface (UIF) sub-system 160 comprising user interfaces devices such as keyboard 162, mouse 164, joystick 166, display 168, and similar input or output devices. Display 168 also shows real-time image information acquired by the imaging system 150 and localization information acquired by the three-dimensional localization system. UIF sub-system 160 relays inputs from the user to a navigation sub-system 170 comprising 3D localization block 172, feedback block 174, planning block 176, and controller 178. Navigation control sequences are determined by the planning block 176 based on inputs from the user, and also possibly determined from pre-operative or intra-operative image data and localization data from a localization device and sub-system and processed by localization block 172, and alternatively or additionally real-time imaging or additional feedback data processed by feedback block 174. The feedback block 174 can in some cases include one or more of the various contact estimation and optimization methods described in the following. The navigation control sequence instructions are then sent to controller 178 that actuates interventional device 120 through actuation block 140 to effect device advance or retraction and tip deflection. Other navigation sensors might include an ultrasound device or other device appropriate for the determination of distances from the device tip to surrounding tissues, or for tissue characterization. Further device tip feedback data may include relative tip and tissue positional information provided by a local intra-operative imaging system, and predictive device modeling and representation. Such device feedback in particular enables remote control of the intervention.

In closed-loop implementations, the navigation sub-system 170 automatically provides input commands to the device advance/retraction 142 and tip orientation 144 actuation components based on feedback data and previously provided input instructions; in semi closed-loop implementations, the physician fine-tunes the navigation control, based in part upon displayed information and possibly other feedback data, such as haptic force feedback. Control commands and feedback data may be communicated from the user interface 160 and navigation sub-system 170 to the device and from the device back to navigation sub-system 170 and the user through cables or other means, such as wireless communications and interfaces. Additionally, FIG. 6 schematically shows "remote navigation interventional procedure" block 180 that performs specific functions in various embodiments of the present invention. Block 180 applies to magnetic navigation system such as that illustrated in FIG. 6, and more generally to any medical navigation device and actuation method that also comprises contact sensing/estimation and enhancement, as described in this disclosure.

Figure 1A:
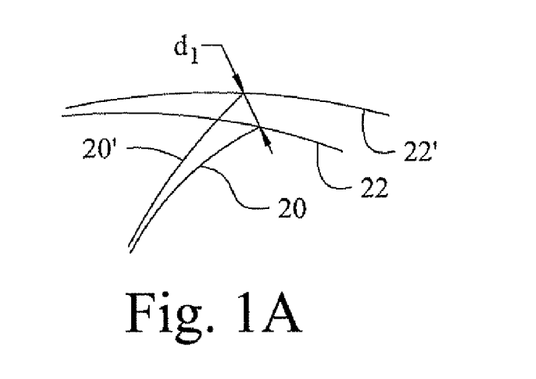
FIG. 1A is a schematic diagram showing a medical device in contact with a cyclically moving anatomical structure (e.g., a heart wall) illustrating good contact as the device moves a distance $d_1$ to remain in contact over the cycle of movement.
Figure 1B:
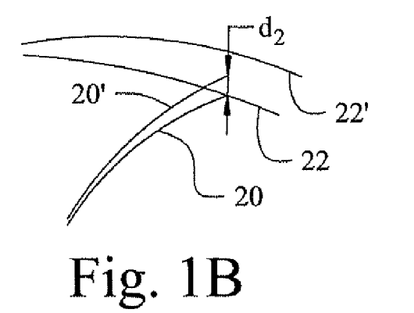
FIG. 1B is a schematic diagram showing a medical device in contact with a cyclically moving anatomical structure (e.g., a heart wall) illustrating poor contact as the device moves a distance $d_2$ and loses contact over the cycle of movement.

In accordance with another embodiment of this invention, real-time tip location data can also be used to estimate the qualitative extent of contact with an anatomical structure. The inventors have discovered that a catheter with a soft shaft (such as magnetic catheters) that is engaged in wall contact will tend to maintain tip contact at a fixed location relative to the cardiac wall during motion of the wall, since the shaft can easily buckle or deform to permit this. Accordingly, the extent of motion of the tip over the cardiac cycle will be largest when contact is very consistent. This is illustrated in FIGS. 1A and 1B, where in FIG. 1A, the medical device 20 is in good contact and remains in contact with the moving anatomical surface 22 during the entire cycle. Thus midway through the cycle, the medical device 20' is still in contact with the surface 22', and the device 20 has a total displacement $d_1$ corresponding to the movement of the surface 22. As shown in FIG. 1B where the medical device is not in good contact, the tip loses contact with the anatomical surface. At the start of the cycle the tip 20 is in contact with anatomical surface 22, and midway through the cycle medical device 20' loses contact with the surface 22, and the device has a total displacement $d_2$ that is less than the total movement of the surface 22. The motion of the medical device is such that $d_1 > d_2$, so that greater device motion corresponds to better contact, and this can be used in several ways to estimate the quality of contact of the device with the anatomical structure.

Figure 2A:
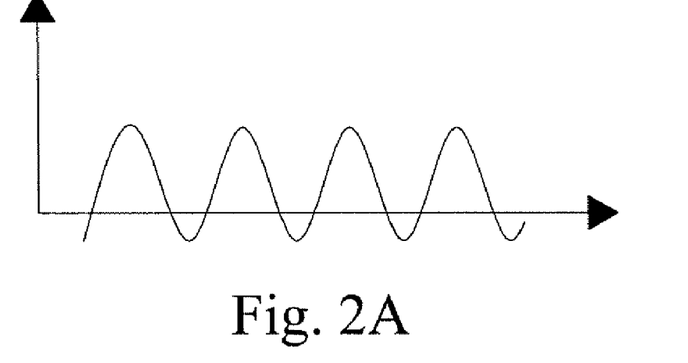
FIG. 2A is a graph of $x_{real} - x_{gated}$ for a medical device in contact with an cyclically moving anatomical structure, over several motion cycles, showing substantially continuous movement indicative of good device contact.
Figure 2B:
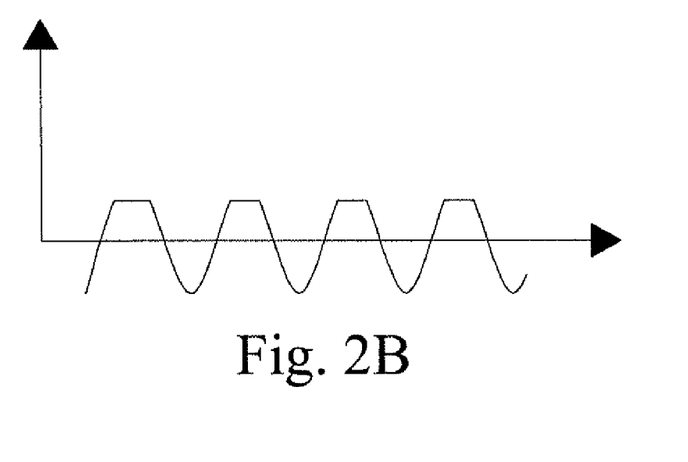
FIG. 2B is a graph of $x_{real} - x_{gated}$ for a medical device in contact with an cyclically moving anatomical structure, over several motion cycles, showing discontinuous or truncated movement indicative of poor device contact.

One way of estimating the quality of contact is using the oscillation amplitude. The oscillation of the difference $[x_{real} - x_{gated}]$ can be tracked over a few cardiac cycles, where the three dimensional vectors are defined such that $x_{gated}$ is always the most recent gated location (gated to the cardiac cycle) and $x_{real}$ is the realtime location. If the contact is good, the distal tip of the device moves with the movement of the surface, and the graph of the oscillation shows a relatively smooth and continuous movement (as shown in FIG. 2A). If contact is temporarily lost for a portion of time between successive cycles, the amplitude of the oscillation will display a "truncated" or flat behavior over such time intervals (as shown in FIG. 2B), where the catheter location will stay relatively constant, and this can be detected from signal analysis to assess stability of contact.

Figure 3:
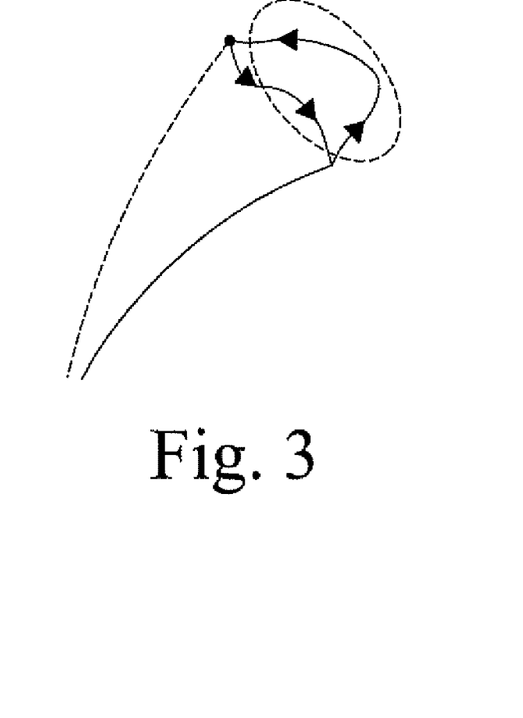
FIG. 3 is a schematic diagram showing the movement of the distal tip of a medical device that is in contact with a cyclically moving anatomical structure, together with the constructed covariance ellipsoid in dashed lines.

Another way of estimating the quality of contact is using positional covariance. If $x_{mean}$ is the mean location over a cardiac cycle, set $X=(x-x_{mean})$ and form the 3×3 covariance matrix C with entries $C_{ij}=\langle X_i X_j \rangle$ where the average $\langle \ \rangle$ is taken over a cardiac cycle (or over several cycles). Let a, b and c be the eigenvectors of C, with corresponding eigenvalues $e_a$, $e_b$, $e_c$. These eigenvectors and eigenvalues define the covariance ellipsoid associated with the motion of the catheter tip (as shown in FIG. 3). A soft catheter that maintains good contact with a given target location on the cardiac wall over the cardiac cycle will have larger values of ($e_a$, $e_b$, $e_c$) than a catheter that is in inconsistent/unstable contact; thus for example, $D=(e_a+e_b+e_c)$ can be used as a measure of contact.

Alternative measures based on the eigenvalues of the positional covariance matrix can also be constructed. Thus, alternatively or in addition to the measure D given above, the difference between maximum and minimum eigenvalues ($e_{max}-e_{min}$) can be used as a measure of contact; in some situations a larger eigenvalue difference can represent greater relative motion along one direction, thus characterizing the local cardiac wall motion. For example the cardiac ventricles exhibit expansion and contraction in volume together with a strong twisting wall motion; this leads to a local wall motion pattern that can be generally termed an elongated approximate ellipse. A catheter tip in stable contact with such a cardiac wall location would move with the cardiac wall through the cardiac cycle.

Figure 4:
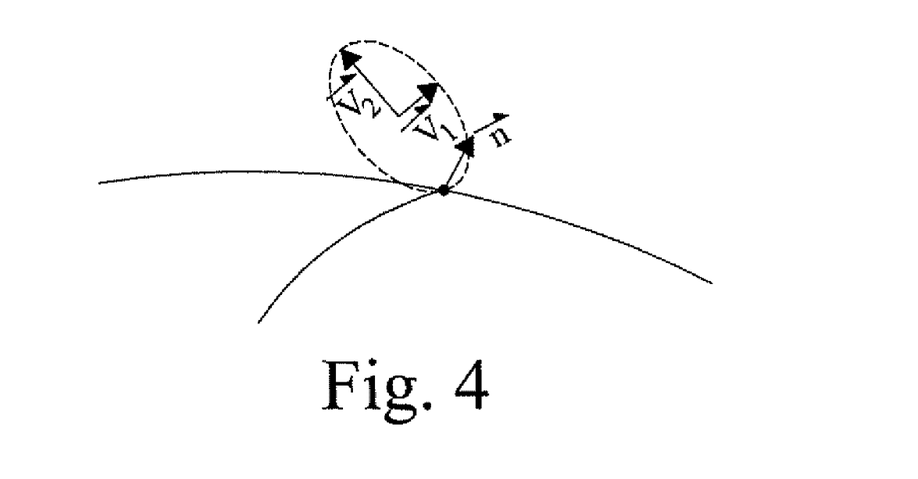
FIG. 4 is a schematic diagram showing a co-variance ellipsoid and two of its axes $\vec{v}_1$ and $\vec{v}_2$ are shown.

To enhance contact between the medical device and the tissue, the surface normal n to the cardiac wall can be used in order to torque the device tip into the wall. For example, with a magnetic navigation system, the magnetic field can be rotated about an axis defined by v=t×n in order to push the device tip into the wall, where t is the device tip orientation. In this case, let a be the eigenvector of C that has the largest dot product with n ($\vec{v}_1$ in FIG. 4); then a can be used in some cases place of n to define the axis of rotation v. While this is useful in magnetic navigation, it can also be exploited with other navigation systems.

Another way of estimating the quality of contact is using orientational covariance. If $t_{mean}$ is the mean tip orientation over a cardiac cycle, and $T=(t-t_{mean})$, a covariance matrix M can be formed with entries $M_{ij}=\langle M_i M_j \rangle$ (average taken over a cardiac cycle), and as with the positional covariance matrix discussed above, the eigenvalues and eigenvectors of M can be used to assess extent of contact. Analogously to the contact measures based on positional covariance eigenvalues, various measures based on the orientational covariance eigenvalues such as the magnitude of the summed eigenvalues, or the difference between maximum and minimum eigenvalues, can be used to assess stability of cardiac contact.

Another method of measuring contact stability is to perform a frequency analysis of catheter tip motion. The frequency spectrum of the motion of a catheter tip that is in firm contact with the cardiac wall will have a dominant peak at the frequency of the cardiac cycle. Thus, the ratio of the peak (maximum, or dominant frequency) in the Fourier transform of the catheter tip location over a period of time to the next smaller peaks (the sub-dominant peaks) in the frequency spectrum can provide a measure of contact and can in a sense be interpreted as a Signal-to-Noise ratio. The frequency spectrum of the tip position will have to be obtained in general from motion over multiple cardiac cycles, and can be obtained from applying the Fourier transform to the tip position data. The amplitude of the heart rate frequency should be greater with more consistent contact and less with less consistent myocardial contact. More consistent contact should be conveyed by a greater signal-to-noise ratio as the tip moves with the myocardium, and vice-versa. Filtering the tip position data prior to implementing these algorithms can be implemented as a preprocessing step and can lead to improved quantification of contact stability. Of course, it will be important to apply the filter at least several beats prior to the cardiac cycle being analyzed to allow the transient effects of the filter to decay sufficiently. Other measures based on the frequency spectrum such as the spread in frequency between specified peak threshold values, or a variety of other such possible measures that can be determined by those skilled in the art can also be used without limitation and the specific examples of measures detailed here are provided for illustrative purposes only.

Figure 5A:
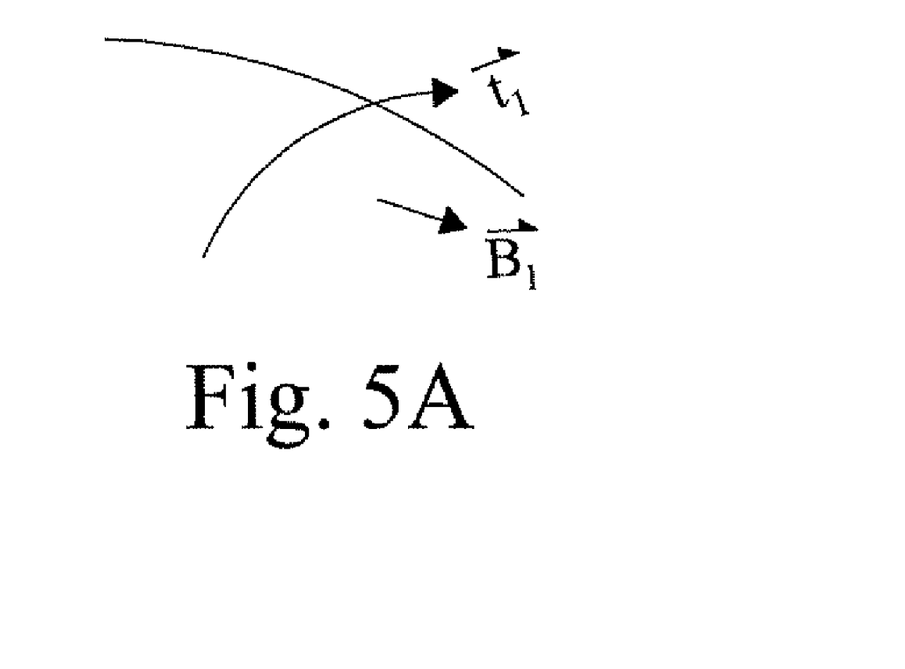
FIG. 5A is a schematic diagram showing a magnetically navigated medical device with an applied magnetic field $\vec{B}_1$ with a tip orientation $\vec{t}_1$, against the cardiac wall.
Figure 5B:
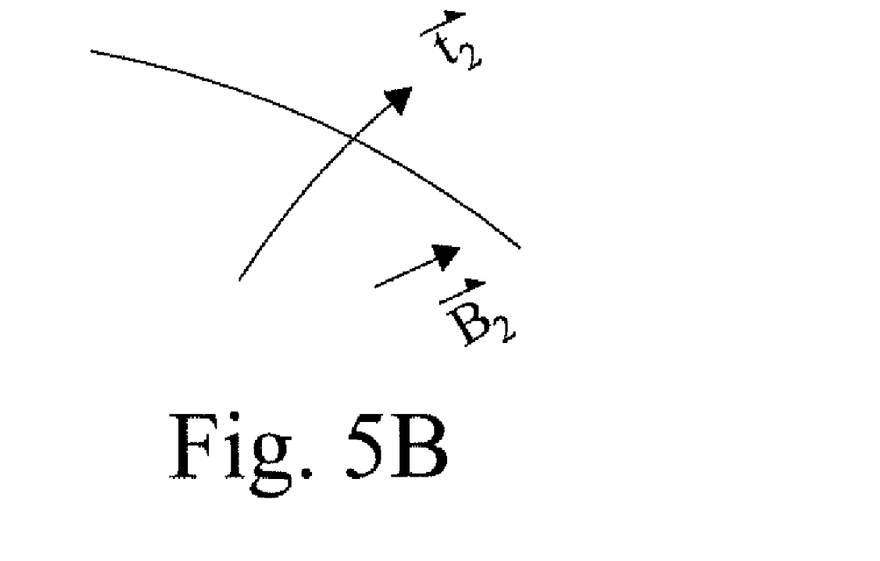
FIG. 5B is a schematic diagram showing a magnetically navigated medical device with an applied magnetic field $\vec{B}_2$, different from field $\vec{B}_1$, resulting in a tip orientation $\vec{t}_2$.

Another way of estimating the quality of contact is using perturbation. A control variable of the navigation system (for example magnetic field direction, or catheter insertion length) can be perturbed or changed by a small amount, and the resulting change in a contact measure (such as one of the eigenvalue-based measures discussed above) can be determined. Thus for instance if contact is found to be enhanced by a small amount, a larger change in the same sense of the corresponding control variables can be applied to further enhance contact. As shown in FIG. 5A, the tip orientation $\vec{t}_1$ is determined with a particular control value, for example the applied magnetic field $\vec{B}_1$. As shown in FIG. 5B, the control variable is changed, for example from $\vec{B}_1$ to $\vec{B}_2$, and the resulting changing in tip orientation $\vec{t}_2$ is evaluated, to determine the control variable that provides the optimum, or at least the local maximum, contact.

Another way of estimating the quality of contact is using unipolar voltage: If unipolar intracardiac ECG voltage information is available in real-time, its magnitude can be used to sense proximity to the wall. In particular, its behavior over a cardiac cycle or a several cycles can be analyzed as in the methods above (except that voltage values would be used instead of positional data) in order to assess stability, with the difference that the variation in voltage will be the smaller when contact is better.

Still another way of estimating the quality of contact is using a mapped mechanical model. A cardiac mechanical motion model is constructed by mapping over a "coarse" set of cardiac wall locations with a localized mapping catheter, so that the range of wall motion at every map point is recorded at each of these locations. Then the range of mechanical motion at intermediate points can be estimated, for example by interpolation. When the catheter is later placed at such an intermediate location, the range of motion as seen in the real-time location data can be compared with the expected range of motion in order to assess quality of contact, so that the closer the actual range is to the expected range, the better the contact quality.

While one method of remote actuation involving applied magnetic fields has been described for illustrative purposes, other methods of remote actuation can be involved in the remote navigation control, such as mechanical operation using a set of motorized pull-wires, electrostrictive actuation, hydraulic actuation, and various other actuation schemes known to those skilled in the art. In one embodiment the directly actuated device can be a hollow sheath that carries through it another device or devices.

Thus the various embodiments of this invention provide for the improved control, and in particular for enhanced measure of contact, and thus control of contact, of a remote medical navigation system. Any method of remote navigation can be implemented. Likewise a variety of contact measures can be constructed by those skilled in the art according to the concepts taught in this invention. These and other features and advantages will be in part apparent, and in part pointed out hereinafter, and the scope of the invention is limited only by the appended claims.

What is claimed:

1. A method of enhancing contact between a cyclically moving anatomical structure and a remotely navigated medical device, the method comprising determining a covariance matrix based upon the difference between the actual location and the mean location over the cyclical movement;
   determining the eigenvectors of the covariance ellipsoid associated with the motion of the device tip;
   identifying the eigenvector $e_a$ of the covariance matrix that has the largest dot product with the surface normal vector n at the point of contact between the device and the anatomical surface; and
   rotating the device about the eigenvector $e_a$ to increase contact between the device and the anatomical surface.

2. The method of claim 1, where the remotely navigated device is magnetically actuated.

3. The method of claim 1, where the remotely navigated device is mechanically actuated.

4. The method of claim 1, where the remotely navigated device is electrostrictively actuated.

5. A method of determining contact stability of a remotely navigated medical device whose distal tip region is in contact with a cyclically moving anatomical structure, the method comprising:
   recording the spatial motion of the distal tip of the medical device through sampling location data over a time period of at least two motion cycles;
   determining the Fourier frequency spectrum of the spatial motion to identify at least one dominant frequency of the spatial motion; and
   constructing a measure of contact stability of the medical device from analysis of the Fourier frequency spectrum.

6. The method according to claim 5 where the step of identifying at least one dominant frequency of the spatial motion includes identifying at least one sub-dominant peak in addition to the most dominant peak of the spatial motion.

7. The measure according to claim 6 where the most dominant peak and at least one sub-dominant peak in the Fourier frequency spectrum are used in constructing the measure of contact stability.

8. The method of claim 7, where the measure of the contact stability is a ratio of the most dominant peak to the sub-dominant peak.

* * * * *